US011852796B2

(12) United States Patent
Abdennour et al.

(10) Patent No.: US 11,852,796 B2
(45) Date of Patent: Dec. 26, 2023

(54) BINOCULAR OPERATING MICROSCOPE PROTECTIVE SHIELD BARRIER

(71) Applicants: Tom C. Pagonis, Chestnut Hill, MA (US); Mario Abdennour, North Andover, MA (US)

(72) Inventors: Mario Abdennour, North Andover, MA (US); Tom C. Pagonis, Chestnut Hill, MA (US)

(73) Assignee: Pagonis/Abdennour

( * ) Notice: Subject to any disclaimer, the term of this patent is extended or adjusted under 35 U.S.C. 154(b) by 224 days.

(21) Appl. No.: 17/318,700

(22) Filed: May 12, 2021

(65) Prior Publication Data

US 2021/0356727 A1 Nov. 18, 2021

Related U.S. Application Data

(60) Provisional application No. 63/023,419, filed on May 12, 2020.

(51) Int. Cl.
| G02B 21/00 | (2006.01) |
| G02B 21/22 | (2006.01) |
| A61B 46/00 | (2016.01) |
| A61B 46/10 | (2016.01) |

(52) U.S. Cl.
CPC .............. G02B 21/22 (2013.01); A61B 46/10 (2016.02); A61B 46/40 (2016.02); G02B 21/0012 (2013.01)

(58) Field of Classification Search
CPC ........................... G02B 21/00; G02B 21/0004; G02B 21/0008; G02B 21/0012; G02B 21/0016; G02B 21/0028; G02B 21/20; G02B 21/22; G02B 7/00; G02B 7/12; G02B 7/20; G02B 7/21; G02B 23/00; G02B 23/16; G02B 23/18; G02B 23/22; G02B 23/2476; G02B 23/2493; G02B 27/00; G02B 27/0006; A61B 46/10; A61B 46/40
USPC ................. 359/368, 407–412, 507–514, 600
See application file for complete search history.

(56) References Cited

U.S. PATENT DOCUMENTS

| 4,183,613 A * | 1/1980 | Walchle ................. A61B 46/10 |
| | | 359/510 |
| 4,618,222 A * | 10/1986 | Eisenberg .......... G02B 21/0016 |
| | | 359/507 |
| 10,175,467 B2 * | 1/2019 | Mazel .................... G02B 21/24 |
| 11,287,639 B2 * | 3/2022 | Jones ..................... A45C 11/08 |

(Continued)

OTHER PUBLICATIONS

Api, anthony products, inc., Reusable Faceshield for Microscope, Item No. JM-98-1955. Retrieved online at: https://www.anthonyproducts.com/store/reusable-faceshield-for-microscope. 4 pages, (2021).

(Continued)

*Primary Examiner* — Thong Q Nguyen
(74) *Attorney, Agent, or Firm* — McCarter & English, LLP

(57) ABSTRACT

A device for protecting a dental professional from patient aerosol and splatter is provided. The device includes a first elastic section with two holes connected to a second rigid section. The first section is sufficiently elastic to allow for increasing or decreasing the inter optic distance of a binocular operating microscope without affecting the seal or material integrity of the first section or the position or function of the second section.

7 Claims, 7 Drawing Sheets

(56) References Cited

U.S. PATENT DOCUMENTS

2021/0346113 A1* 11/2021 Nuzum ................. A61B 90/05
2022/0061954 A1* 3/2022 Madow ................. A61B 46/10

OTHER PUBLICATIONS

ChinRestPaperSource, Breath shield for ophthalmic, dental, ENT Surgical Microscope, Curved, Thick Acrylic. Retrieved online at: https://chinrestpapersource.com/AMBMU. 12 pages, (2021).
Shieldont, Shieldont for Other Microscope Brands. Retrieved online at: https://www.shieldont.com/products/shieldont. 5 pages, (2021).
Zeiss, Seeing more with the first digital microscope. Zeiss Artevo 800. Retrieved online at: zeiss.com/artevo800. 12 pages, (2019).

* cited by examiner

BINOCULAR OPERATING MICROSCOPE PROTECTIVE SHIELD BARRIER

This Application claims the benefit of U.S. Provisional Application 63/023,419 filed on May 12, 2020. The entire contents of the '419 application is incorporated herein by reference in its entirety.

FIELD OF THE INVENTION

The present disclosure relates to a clinical operator (dentist, endodontist or other health care professional) personal protective device with material, positioning and mounting systems for use with a binocular operating microscope during a clinical examination or operation.

BACKGROUND

The production of human aerosol during dental and endodontic procedures is a significant issue in matters of infection control and disease transmission. An aerosol is the airborne cloud of particulate matter, fluid (including saliva) and blood that is clearly visible particularly during the preparation (i.e. drilling) of tooth structure. During a dental operation airborne viruses and bacteria including *viridans* streptococci and staphylococci from aerosol and patient splatter will contaminate a dentist, dental auxiliary personnel and their personal protective equipment (PPE) with significant contamination at great distances beyond the operating field and throughout the entire dental operating room. With the advent and recent spread of severe acute respiratory syndrome coronavirus 2 (SARS-CoV-2), questions concerning the potential for spread of the disease from aerosolized blood, saliva and splatter of infected patients have arisen. The Centers for Disease Control (CDC) recommends an upgrade in personal protective equipment (PPE) by dentists and endodontists for increased protection from smaller respiratory droplets of potentially infected COVID-19 patents. These upgrades include changing from level 3 surgical masks to NIOSH-approved N95 masks, the use of full facial protection by way of goggles or a face shield and the continuous use of gowns and gloves. The use of PPE greatly mitigates but does not eliminate the risk of disease transmission. However dentists and endodontists utilizing enhanced visualization or the use of a binocular operating microspore are subject to greater risk because the use of enhanced PPE such as goggles or a face shield is ergonomically very difficult or even not possible while using a binocular operating microscope during a dental operation. These disease transmission concerns and accompanying infection control challenges are also prevalent among ophthalmologists, optometrists and other healthcare professionals that perform examinations or clinical operations close to a patient when utilizing all types of binocular operating microscopes.

The utilization of PPE barriers does not address protection from bacteria and viruses produced from patient splatter and aerosol while a dentist or endodontist is operating under a binocular operating microscope.

SUMMARY

Exemplary embodiments are directed towards a protective shield barrier comprised of multiple materials that universally adapts and mounts to a binocular operating microscope, provides a seal around each viewing optic of the microscope, allows adjustment of binocular interpupillary distance and provides protection from patient splatter and aerosol for the dentist, endodontist or other healthcare professional viewing through the binocular operating microscope or directly visualizing the operating site and patient during a dental or other operation.

In accordance with an aspect of the present disclosure for closely adapting to and sealing around each optic of the binocular operating microscope, a flexible/elastic rubber section (latex, nitrile or similar) with two pre-punched holes is provided. Each rubber section provides pre-punched holes of smaller diameter than each binocular operating microscope optic diameter. Each optic of the binocular operating microscope is placed through each corresponding pre-punched hole of the device disclosure or shield barrier and tightly adapts around each corresponding optic once the device disclosure is mounted. The elasticity of the material in this rubber section tightly seals around the periphery of each corresponding optic and allows the dentist or other healthcare professional to utilize the optic capabilities of the binocular operating microscope during a dental or other operation.

Embodiments of the above exemplary device can include one or more of the following. In some embodiments, the highly elastic rubber section of the present disclosure provides enhanced protection from patient splatter and aerosol by sealing around the binocular operating microscope optics during an operation. In one embodiment, the material elasticity in the rubber section of the device allows adjustment of the binocular operating microscope inter optic distance to correspond to each individual dentist's (or other health care professional) interpupillary distance which varies from person to person and is defined as the distance measured in millimeters between the centers of the pupils of the eyes. In another embodiment, adjusting the binocular operating microscope interpupillary distance either by increasing the distance or decreasing the distance does not affect the sealing capabilities of the material in the rubber section, does not affect the material integrity of the rubber (latex, nitrile or similar) section, does not affect the device function in the binocular operating microscope positioning and does not diminish the device's ability to protect a dentist (or other healthcare professional) from patient splatter and aerosol. In another embodiment, the seal created by the tightly adapted elastic material of the rubber section around the optics provides protection from patient aerosol and splatter.

In accordance with another aspect of the present disclosure, further disclosed is a larger, transparent rigid (plastic, acetate or similar) section surrounding and attaching to or integrated with the smaller and more elastic rubber section which, as previously noted, is used for adapting to the optics of the binocular operating microscope. The present device disclosure therefore includes a smaller, elastic or non-rigid rubber (latex, nitrile or similar) section located approximately in the center surrounded by a transparent rigid (plastic, acetate or similar) section.

Embodiments of the above device disclosure can include one or more of the following. In some embodiments the transparent peripheral and larger rigid (plastic, acetate or similar) section provides necessary structure to create a stable and rigid shield barrier against patient splatter and aerosol during a dental or other operation. In some embodiments the adaptation and adherence of the rubber section to the rigid section maintains the necessary rigidity to stay mounted in place, allows for proper positioning of the entire device, and creates customized sealing of the optics of a binocular operating microscope from potential patient aerosol or splatter with a capability of adjusting interpupillary distance of all binocular operating microscopes. In some embodiments the larger rigid section provides protection above and below the optics of a binocular operating microscope thereby protecting the dentist's (or other healthcare professional) head and chest from aerosol and splatter during a dental or other examination or operation. In some embodiments the entire device disclosure provides the dentist or endodontist protection from patient aerosol and splatter. In some embodiments the size of the device disclosure provides protection of the dentist, allows for direct visualization of the operating site and allows for direct visualization and monitoring of a patient during a dental operation. These embodiments also apply to other health care professionals utilizing a binocular operating microscope during patient care. These embodiments also apply to laboratory professionals utilizing a binocular operating microscope during research.

The exemplary device of the present disclosure provides several advantages. For example, the disclosed device yields an additional personal protective piece of equipment for a binocular operating microscope clinician (operator) in order to mitigate the risk of disease transmission from patient aerosol and splatter. Further the device disclosed herein offers a multiple material personal protective equipment with custom adaptation to, and adjustment of, any binocular operating microscope optics. In the device disclosed herein protection from patient aerosol or spatter greatly improves a dentist's or endodontist's ability to properly utilize a binocular operating microscope by forgoing the use of bulky and ergonomically burdensome goggles and face shields. In the device disclosed herein a mounting and stable positioning apparatus is available for a binocular operating microscope. In the device disclosed herein a dentist or endodontist is able to directly operate a binocular operating microscope or directly visualize and monitor both the patient and the operating site. The advantages of exemplary device of the present disclosure are afforded to and apply to other healthcare professionals utilizing a binocular operating microscope during patient care.

BRIEF DESCRIPTION OF DRAWINGS

The forgoing and other features and advantages provided by the present disclosure will be more fully understood from the following description of exemplary embodiments when read together with the drawings in the accompanying Figures in which.

DETAILED DESCRIPTION

Provided herein are exemplary embodiments directed to a personal protective device or shield barrier for a dentist, endodontist or other healthcare professional to be used during an endodontic, other dental or medical examination or operation. The device disclosure is intended for and is easily mounted to a binocular operating microscope. The device is capable of universally adapting to all binocular operating microscopes, providing a seal around each optic of all binocular operating microscopes, providing an option of adjusting optics of a binocular operating microscope including adjustments to interpupillary distances, maintaining a stable, transparent shield barrier thereby providing protection to a dentist, endodontist or other healthcare professional including the entire head and chest from patient aerosol or splatter thus providing the option of not using eye goggles or face shields which are ergonomically difficult during the utilization of a binocular operating microscope. The device is capable of allowing a dentist, endodontist or other healthcare professional to operate either with a binocular operating microscope or to directly visualize the examination site, operating site and the patient. Furthermore, the device disclosure is single use and disposable after each dental or other medical examination or operation.

Figure 1:
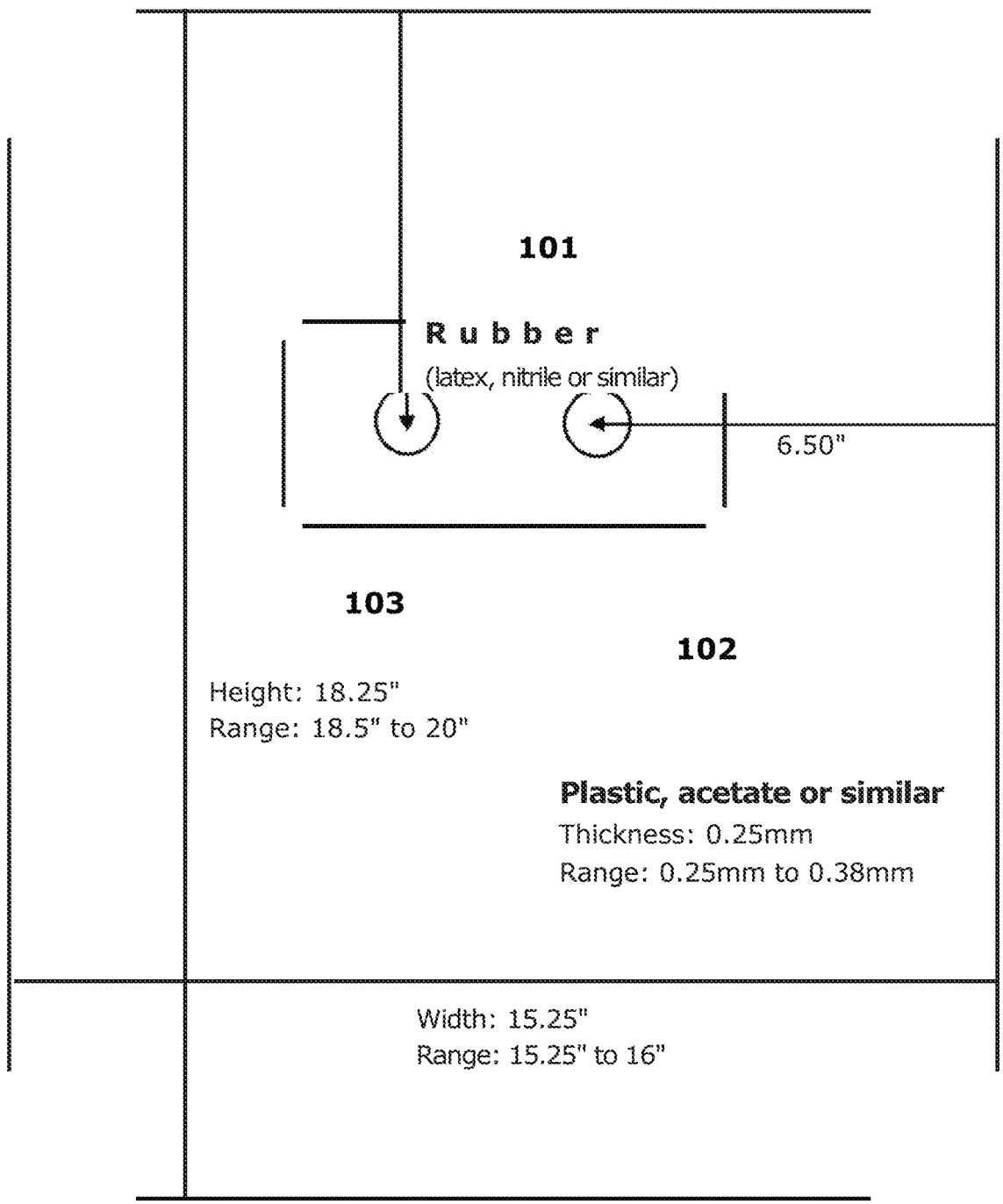
FIG. 1 shows a multiple material shield barrier with dimensions, shape and thickness which is comprised of a rubber first section (101) with holes (103) corresponding to the optics of a binocular operating microscope surrounded by a rigid second section (102).

FIG. 1 is a diagram showing the design, dimensions and materials of the device disclosure. The device is designed to incorporate multiple materials and is comprised of a flexible or elastic rubber (latex, nitrile or similar) section (101) which is located approximately in the center of a surrounding rigid (plastic, acetate or similar) section (102) including a larger area than the rubber section (101). The rubber and rigid sections may be integrated as a single unit. In some embodiments, section (101) is composed of polycarbonate resin thermoplastic. In some embodiments, section (102) is composed of polyurethane.

The rubber section (101) contains two holes (103) which correspond to the optics of a binocular operating microscope. These holes are intentionally slightly smaller in diameter than the corresponding diameter of each binocular operating microscope optics. The elasticity of the material including the holes allows a dentist, dental or other auxiliary personnel to manually expand each hole size with a thumb and index finger thus allowing one to insert or mount the entire device over the individual optics. Once over the individual optics the rubber material is released creating a tight adaptation around the optics of a binocular operating microscope. This seals the optics of binocular operating microscope and protects a dentist, such as an endodontist from patient aerosol or splatter.

In some embodiments, the rigid second section (102) includes at least a portion that is configured to filter orange light. For example, a rectangular filter portion of the rigid second section (102) may include a material that blocks the wavelengths of light corresponding to the color orange. The filter portion allows a dentist or other operator of the device to use the binocular operating microscope without employing additional light sources. The filter portion may be any geometric shape and may encompass a portion, or all of, rigid second section (102).

In alternate embodiments, the rubber section (101) contains one hole (103). In such embodiments, the device is not configured to attach to the optics of a binocular operating microscope. Rather, the device is configured to be oriented parallel to a floor and be attached to a different portion of the microscope (i.e. the housing of the microscope containing the optics, the lens of the microscope).

Figure 2:
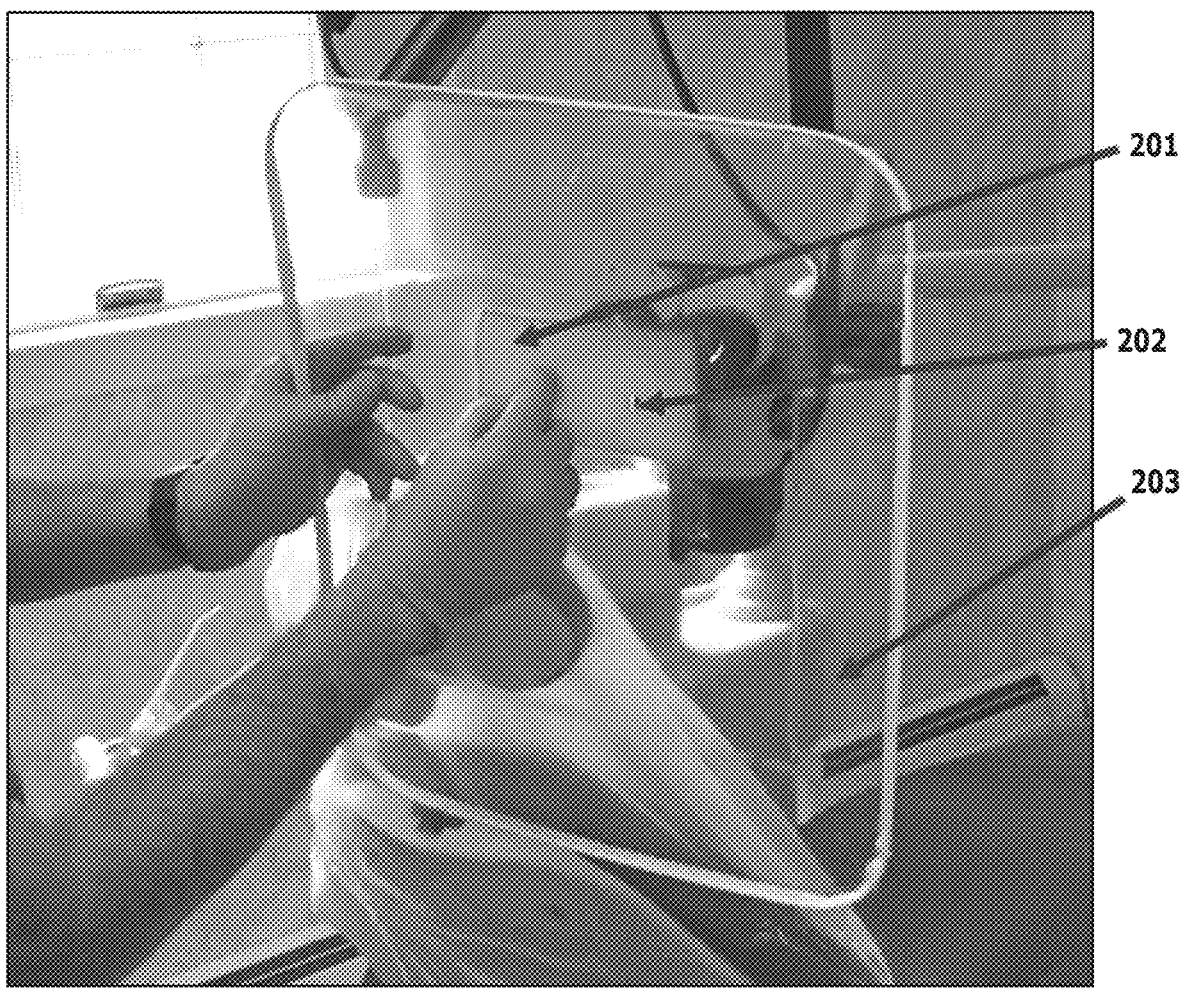
FIG. 2 is the first photograph in a three-photograph sequence designed to illustrate the mounting process of the device disclosure on the individual optics of a binocular operating microscope. It shows the rubber first section of the shield (201), with a hole (202), surrounded by the rigid second section (203).

FIG. 2 is the first photograph in a three-photograph sequence designed to illustrate the mounting process of the device on the individual optics of a binocular operating microscope. It shows the rubber first section (201) of the device, a hole (202) surrounded by the rigid second section (203). Furthermore, the photograph illustrates a dentist's left hand holding the device by the rigid second section (203) with the thumb and index figure of the dentist's right hand approaching one of the holes in the rubber first section (201).

Figure 3:
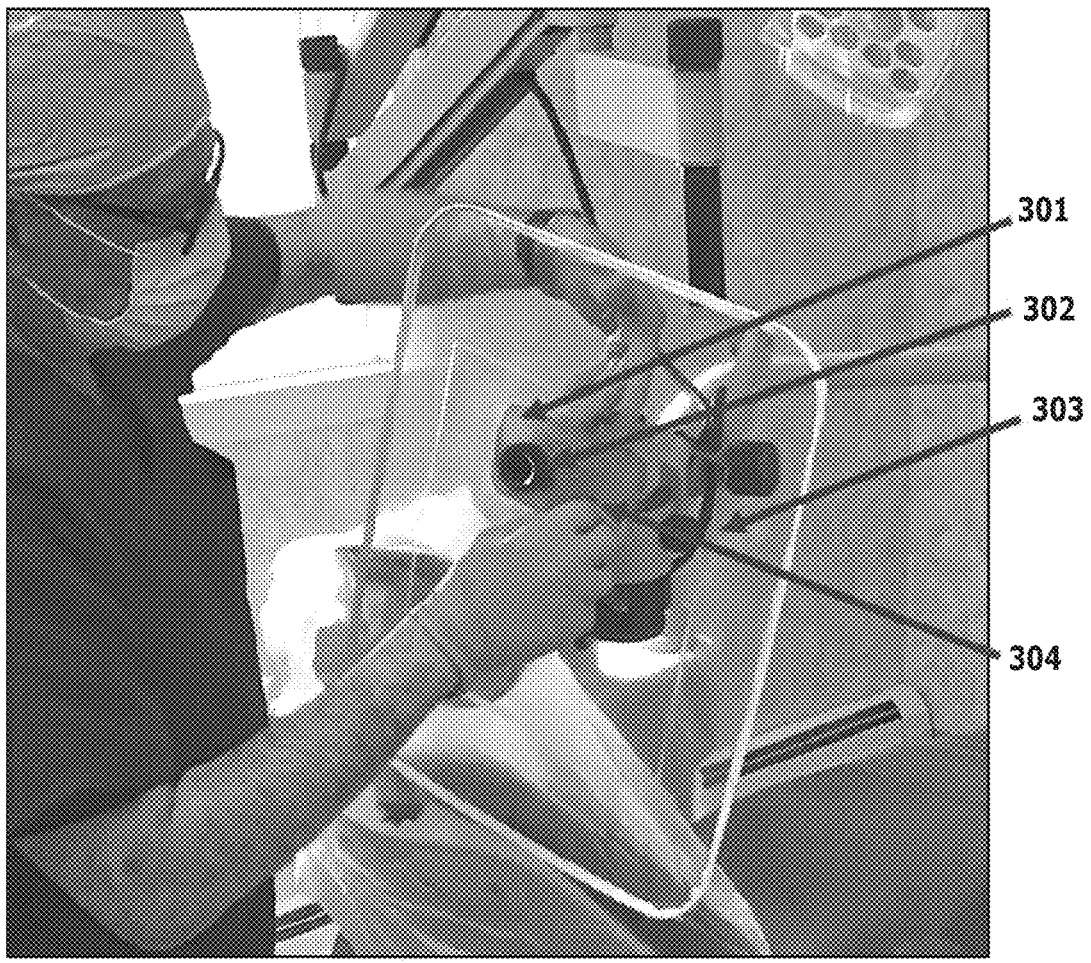
FIG. 3 is the second photograph in the three-photograph sequence designed to illustrate the mounting process of the device disclosure on the individual optics of a binocular operating microscope. It shows the rubber first section of the shield (301), a microscope optic adapted to the hole (302), the surrounding rigid second section (303) of the device and the remaining hole (304) of the rubber first section (301).

FIG. 3 is the second photograph in a three-photograph sequence designed to illustrate the mounting process of the device on the individual optics of a binocular operating microscope. It shows the rubber first section (301) of the device), a hole (302) engaged around one optic of a binocular operating microscope and the surrounding by the transparent rigid second section (303). Furthermore, the photograph illustrates a dentist's left hand holding the device by the rigid second section (303) while the thumb and index figure of the dentist's right hand has engaged, and is beginning to stretch open, the second hole (304) in the rubber first section (301) in order to mount the second or remaining optic of a binocular operating microscope.

Figure 4:
FIG. 4 is the third photograph in the three-photograph sequence designed to illustrate the mounting process of the device disclosure on the individual optics of a binocular operating microscope. It shows the rubber first section of the shield (401), both holes (402) having been engaged around both optics of the binocular operating microscope along with the surrounding rigid second section (403).

FIG. 4 is the third photograph in a three-photograph sequence designed to illustrate the mounting process of the device on the individual optics of a binocular operating microscope. It shows the rubber first section (401) of the device disclosure (barrier shield) with both holes (402) having engaged or having tightly adapted around each individual optic of a binocular operating microscope. In addition, this figure shows the rigid second section (403). Of note, once an optic of a binocular operating microscope is placed through a stretched open hole the tension on the pre-punched hole is released. Once the tension is released the elastic properties of the rubber material snaps back towards its original shape thereby tightly adapting around and sealing the optics of a binocular operating microscope to the rubber first section. To unmount or to remove the device from a binocular operating microscope the rubber first section surrounding each optic is stretched open with a dentist's or dental auxiliary's fingers and the device is pulled away from a binocular operating microscope optics and subsequently disposed.

Figure 5:
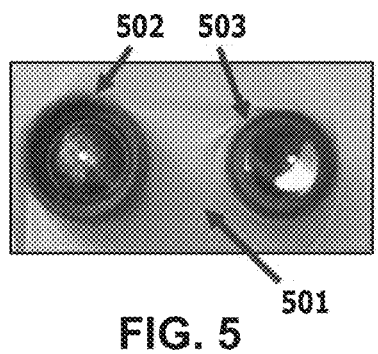
FIG. 5 shows mounting and seal adaptation of the corresponding holes of the rubber first (501) section to the two microscope optics (502), (503) with the distance between optics corresponding to the distance between the holes of the rubber section (501).

FIG. 5 is a photographic closeup of the rubber first section (501) of the device disclosure. It illustrates the tight adaptation or seal that is created over each individual optic (502), (503) of a binocular operating microscope. This figure also illustrates that in some binocular operating microscope designs there is a removable covering on each optic which is temporarily removed and subsequently reattached once the rubber material is adapted around each optic and the device is mounted. The optic to the left (502) illustrates the optic covering in place and the optic to the right (503) shows the optic with the covering removed. This figure also illustrates the material integrity of the rubber section (501) and its function when the distance between optics corresponds to the distance between the holes of the elastic rubber material. Comparing the distance between the holes to the distance between adjustable inter optic distance is designed to illustrate and simulate a possible adjustment to each individual's (dentist or endodontist) inter pupillary distance adjustment.

Figure 6:
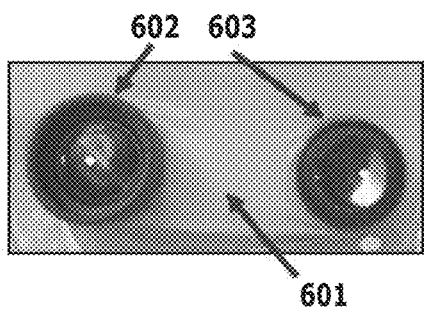
FIG. 6 shows mounting and seal adaptation of the corresponding holes of the rubber first section (601) to the two microscope optics (602) (603) with the distance between optics increased when compared to the corresponding distance between the holes of the rubber first section (601). This action simulates increasing the clinical interpupillary distance with no effect on the seal around the microscope optics and with no effect on the integrity of the elastic material in the rubber section.

FIG. 6 is also a photographic closeup of the rubber first section (601) of the device disclosure. It illustrates the tight adaptation or seal that is created over each individual optic (602), (603). As in FIG. 2, the optic to the left (602) illustrates the optic covering in place and the optic to the right (603) shows the optic with the covering removed. This figure also illustrates the material integrity of the rubber first section and its function when the distance between optics is greater than the distance between the holes of the rubber first section. FIG. 6 is designed to illustrate and simulate an increase in the inter optic distance corresponding to a dentist with an inter pupillary distance greater than the distance between the holes of the rubber section.

Figure 7:
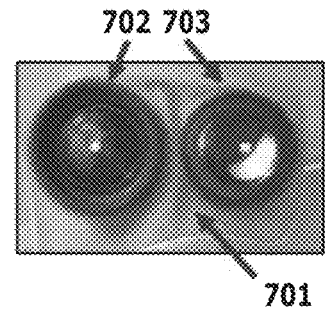
FIG. 7 shows mounting and seal adaptation of the corresponding holes of the rubber first section (701) to the two microscope optics (702) (703) with the distance between optics decreased when compared to the corresponding distance between the holes of the rubber first section (701). This action simulates decreasing the clinical interpupillary distance with no effect on the seal around the microscope optics and with no effect on the integrity of the elastic material in the rubber section.

FIG. 7 is a photographic closeup of the rubber first section (701) of the device. FIG. 7 illustrates the tight adaptation or seal that is created over each individual optic (702), (703). As in FIGS. 2 and 3, the optic to the left (702) illustrates the optic covering in place and the optic to the right (703) shows the optic with the covering removed. This figure also illustrates the material integrity of the rubber first section and its function when the distance between optics is less than the distance between the holes of the rubber section. FIG. 7 is designed to illustrate and simulate a decrease in the inter optic distance corresponding to a dentist with an inter pupillary distance that is less than the distance between the holes of the rubber section.

Figure 8:
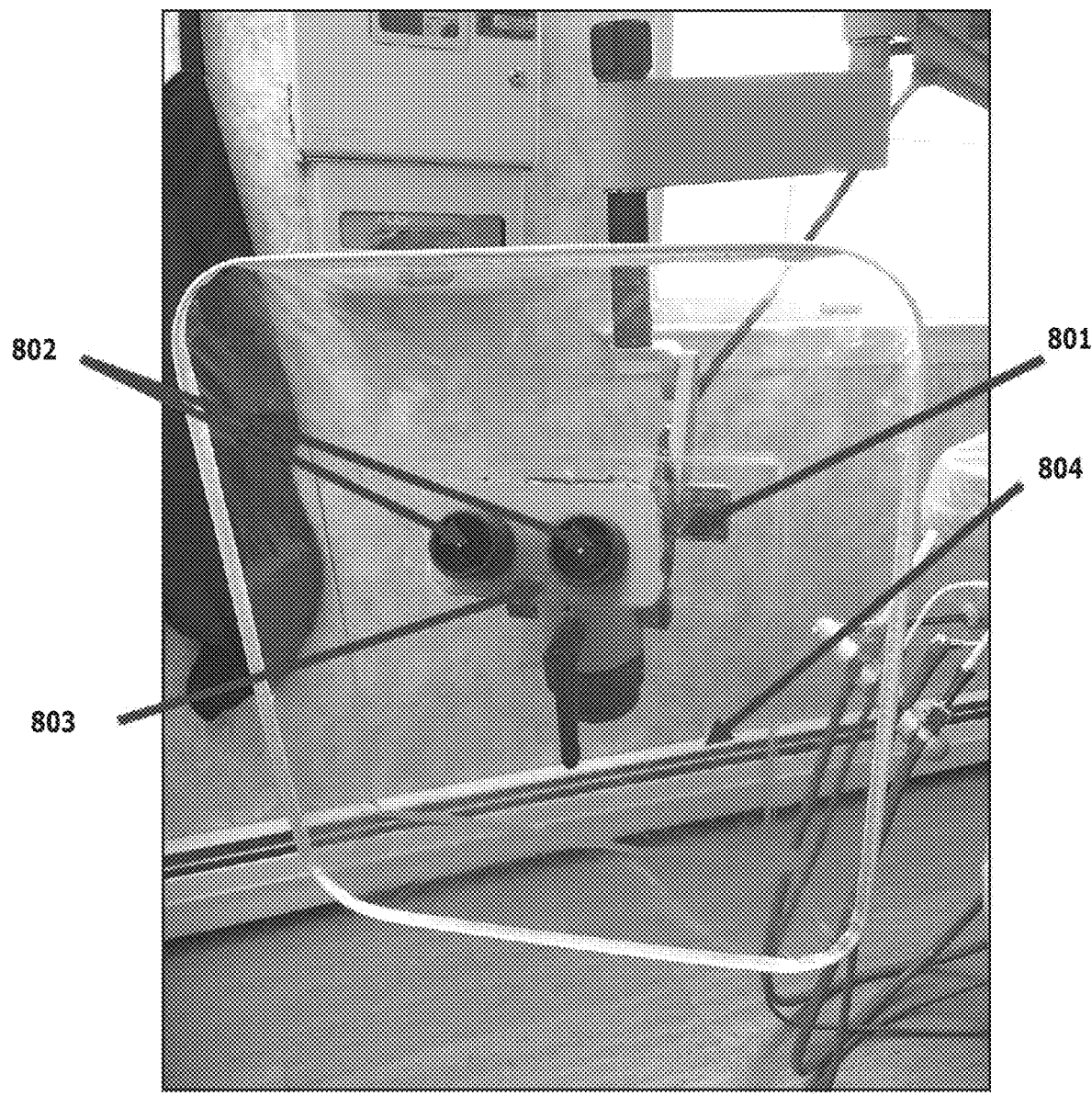
FIG. 8 shows the complete device mounted and positioned on a binocular dental operating microscope (801) and consists of the microscope optics (802) with mounted, sealed and positioned rubber first section (803) of the device (shown in blue). The rubber first section is incorporated within the larger surrounding rigid second section (804).

FIG. 8 is a photographic representation of the entire device disclosure system mounted on a binocular operating microscope (801) and corresponding optics (802). The device, comprised of a smaller rubber first section (803) with holes and surrounded by a larger transparent rigid second section (804) simultaneously leverages both the material flexibility of the rubber first section to create easy and tight adaptations around both optics of a binocular operating microscope and the material rigidity of the surrounding rigid second section to maintain a stable protective barrier to prevent possible disease transmission from a patent aerosol and splatter while a dentist or endodontist is operating under a dental operating microscope.

Figure 9:
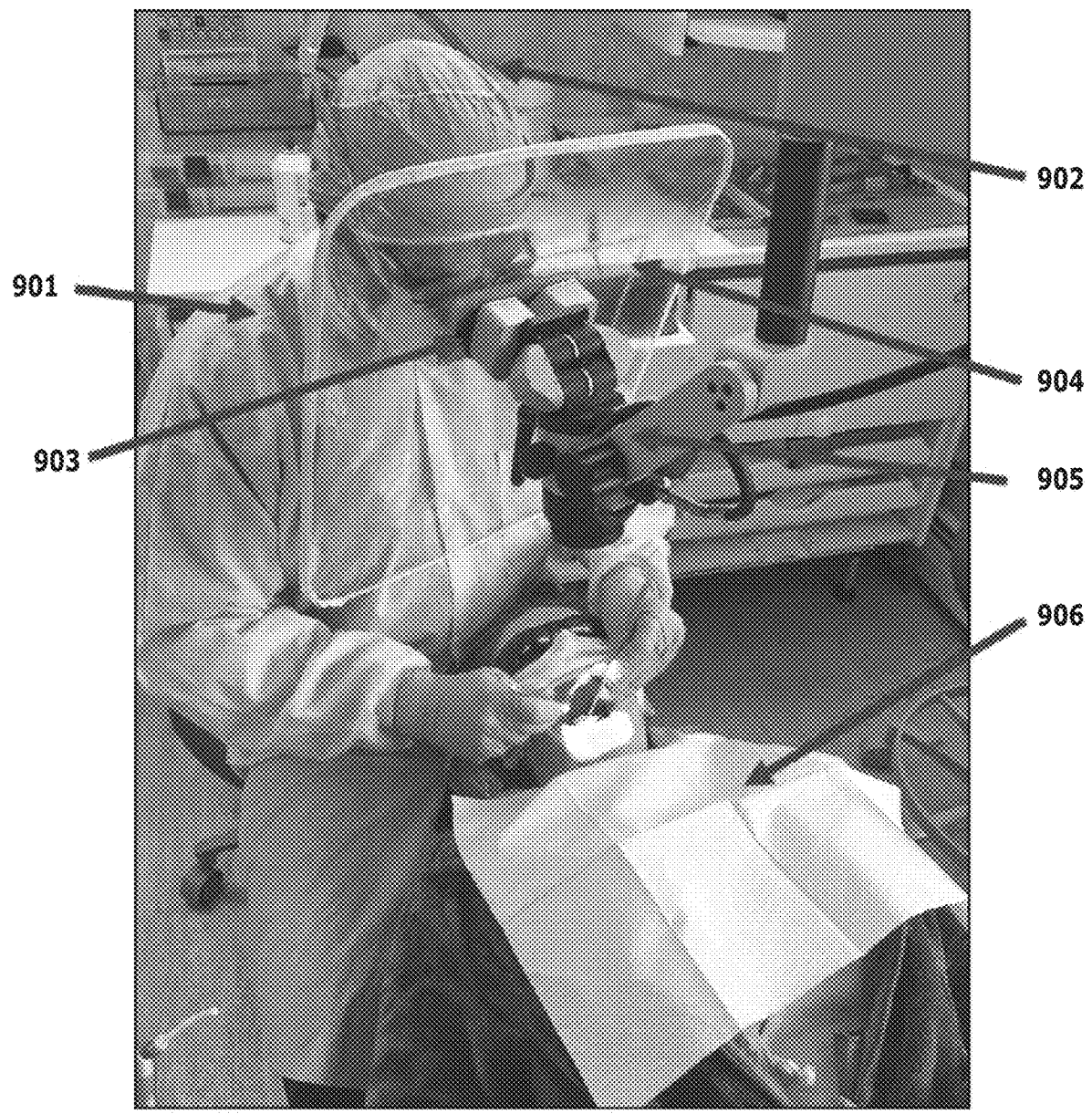
FIG. 9 shows a dentist (901) with a retracted visor of a face shield (902) looking through the optics of a binocular operating microscope with the complete device disclosure mounted and positioned. This figure illustrates the rubber first section (903) of the device disclosure, the larger surrounding rigid second section (904), a binocular operating microscope (905), along with the positioning of the dental patient (906).

FIG. 9 is a photographic representation of a dentist or endodontist (901) with the entire device during a dental operation. Of note, the dentist's face shield visor (902) is raised up and away from the dentist's face as the device disclosure provides adequate protection and because the face shield is ergonomically difficult to use with a binocular operating microscope. The mounted device includes its integrated rubber first section (903) and rigid second section (904) mounted on a binocular operating microscope (905). This photograph illustrates the dentist's ability to seamlessly operate on a patient (906) while utilizing the enhanced visualization of a binocular operating microscope and without the need for ergonomically incompatible eye goggles or face shields. The device disclosure provides protection to the head and chest of the dentist from patient aerosol and splatter. In addition, the transparency of the rigid section allows direct visualization of the operating site and patient.

Figure 10:
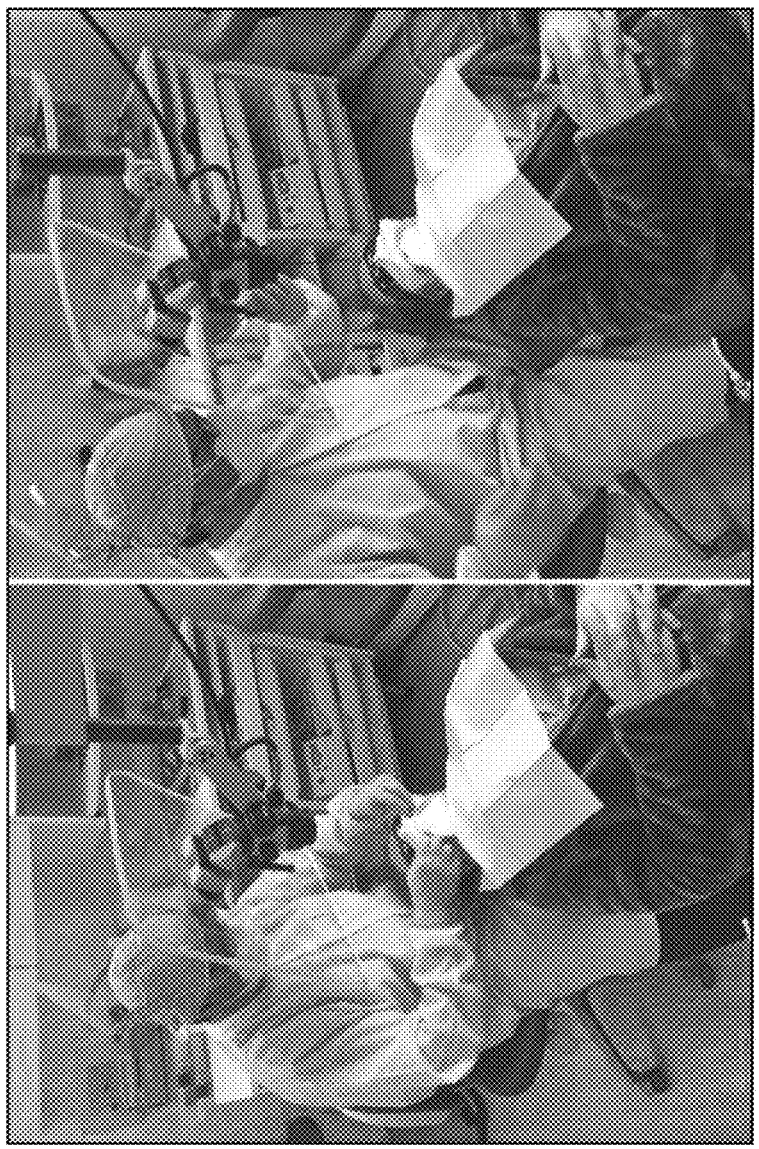
FIG. 10 is a two photograph series of a dentist with the complete device disclosure mounted and positioned on a binocular operating microscope. This figure illustrates the extended protection provided by the device disclosure and the ability or option of a dentist or endodontist to also directly view the operating site and patient during an operation.

FIG. 10 comprises two photographs of a dentist utilizing the entire device during a dental operation. As in FIG. 9 both photographs in FIG. 10 show the face shield visor is raised up and away from a dentist's face as the device disclosure provides adequate protection and because the face shield is ergonomically difficult to use with a binocular operating microscope. The significance of this two photograph series is to illustrate that the device extends above and below the optics of a binocular operating microscope thus providing protection to the head and chest of a dentist or endodontist from patient aerosol and splatter. In addition to and in conjunction with this extended protection, this photographic series illustrates that the transparency of the rigid section allows direct visualization of the operating site and patient by a dentist or endodontist during an operation.

In some embodiments, first section is connected to the second section by a plastic laminate material overlay. The overlay may be rectangular in shape. In some embodiments, the overlay is a component of the first section and is attached to the second section.

While exemplary embodiments have been described herein, it is expressly noted that these embodiments should not be construed as limiting, but rather that additions and modifications to what is expressly described herein also are included within the scope of the invention. Moreover, it is to be understood that many of the features of the various embodiments are not mutually exclusive and can exist in various combinations and permutations, even if such combinations or permutations, are not made express herein, without departing from the spirit and scope of the technology.

The invention claimed is:

1. A device comprising:
a first section comprising an elastic or rubber material with two holes, the first section integrated or attached to a second section comprising a rigid material, creating a protective barrier from debris, fluids, patient aerosol or splatter during a dental operation;
wherein the first section is configured to create a tight adaption and seal around a viewing optics of a binocular operating microscope inserted into the holes;
wherein the first section is sufficiently elastic to allow for increasing or decreasing an inter optic distance of the viewing optics of the binocular operating microscope without affecting the seal or material integrity of the first section or a position or function of the second section.

2. The device of claim 1, wherein the device is an integrated single unit.

3. The device of claim 1, wherein the first section is smaller in area than the second section.

4. The device of claim 1, wherein the first section comprises a latex or nitrile material.

5. The device of claim 1, wherein the second section is transparent.

6. The device of claim 1, wherein the second section comprises a plastic material.

7. The device of claim 1, wherein the first section is located approximately in a center of the second section.

* * * * *